United States Patent [19]

Govil et al.

[11] Patent Number: 5,262,165
[45] Date of Patent: Nov. 16, 1993

[54] TRANSDERMAL NITROGLYCERIN PATCH WITH PENETRATION ENHANCERS

[75] Inventors: Sharad K. Govil, Plantation; Edward M. Rudnic, Boca Raton; Dale G. Sterner, Pembroke Pines, all of Fla.

[73] Assignee: Schering Corporation, Kenilworth, N.J.

[21] Appl. No.: 828,859

[22] Filed: Feb. 4, 1992

[51] Int. Cl.$^5$ .......................................... A61F 13/02
[52] U.S. Cl. ................................. 424/448; 424/449; 424/484; 424/487; 514/946; 514/947
[58] Field of Search ................. 424/448, 449, 484, 487

[56] References Cited

U.S. PATENT DOCUMENTS

| | | | |
|---|---|---|---|
| 3,711,602 | 1/1973 | Herschler | 424/45 |
| 4,291,015 | 9/1981 | Keith et al. | 424/28 |
| 4,305,936 | 12/1981 | Klein | 424/242 |
| 4,322,433 | 3/1982 | Leslie et al. | 424/298 |
| 4,409,206 | 10/1983 | Sticker | 424/81 |
| 4,455,146 | 6/1984 | Noda et al. | 604/897 |
| 4,537,776 | 8/1985 | Cooper | 574/424 |
| 4,557,934 | 12/1985 | Cooper | 424/128 |
| 4,666,441 | 5/1987 | Andriola et al. | 604/897 |
| 4,751,087 | 6/1988 | Wick | 424/449 |
| 4,863,970 | 5/1989 | Patel et al. | 514/784 |
| 4,879,119 | 11/1989 | Konno et al. | 424/449 |
| 5,023,085 | 6/1991 | Francoeur | 514/947 |
| 5,059,628 | 10/1991 | Tsuda | 514/947 |
| 5,079,008 | 1/1992 | Sinnreich | 514/947 |

FOREIGN PATENT DOCUMENTS

| | | |
|---|---|---|
| 0043738 | 1/1982 | European Pat. Off. . |
| 0123948 | 7/1984 | European Pat. Off. . |
| 0179277 | 4/1986 | European Pat. Off. . |
| 0196769 | 10/1986 | European Pat. Off. . |
| 0224981 | 6/1987 | European Pat. Off. . |
| 0261429 | 3/1988 | European Pat. Off. . |
| 0290262 | 11/1988 | European Pat. Off. . |
| 8701935 | 4/1987 | PCT Int'l Appl. . |
| 8703490 | 6/1987 | PCT Int'l Appl. . |
| 2081582 | 2/1982 | United Kingdom . |

OTHER PUBLICATIONS

J. Pharm. Sci, 73, No. 8 (1984) pp. 1153–1156.
J. Pharm. Sci., 64, No. 3 (1975) pp. 397–401.
Transdermal Delivery of Drugs, vol. 1, Chap. 11, A. F. Kydonieu, ed., pp. 145–156.

*Primary Examiner*—Thurman K. Page
*Assistant Examiner*—D. Gabrielle Phelan
*Attorney, Agent, or Firm*—Anita W. Magatti; Eric S. Dicker

[57] ABSTRACT

A transdermal nitroglycerin patch exhibiting superior nitroglycerin skin penetrating characteristics comprising a percutaneous penetration enhancer is disclosed, wherein the penetration enhancer may be one or more of N-methyl-2-pyrrolidone, oleic acid, oleyl butanediol, linoleic acid, isopropyl linoleate, azone and alcohol. Also disclosed is a transdermal patch design comprising two concentric rings, wherein the concentrations of nitroglycerin and the permeability enhancer are varied.

6 Claims, No Drawings

TRANSDERMAL NITROGLYCERIN PATCH WITH PENETRATION ENHANCERS

BACKGROUND OF THE INVENTION

This invention relates to the transdermal delivery of nitroglycerin, in particular to transdermal delivery through the use of penetration enhancers.

Many drugs are destroyed on the first pass through the liver when taken orally. Because metabolism of said drugs is rapid, pharmacological activity and therapeutic effects of such drugs are not constant. In view of such difficulties, a number of different drug delivery systems have been developed. Recently, the use of transdermal delivery systems has met with increasing interest by researchers in the pharmaceutical drug delivery field.

Problems with efficacy arise, however, when using transdermal delivery systems. The device must supply a sufficient amount of the pharmaceutically active ingredient to the patient and a sufficient amount of drug must penetrate the patient's skin in order to obtain the desired pharmacological effect over a given period of time. Different means may be employed to obtain the desired efficacy over that period of time.

One means of attempting to increase the amount of drug delivered might be to include a higher concentration of the pharmaceutically active drug in the delivery system in the hope that by simply increasing the concentration of the drug, the amount of the drug penetrating the skin of the patient may be increased. However, this concept is limited by the amount of drug which can be administered through the skin, i.e., the skin acts as a rate-limitation means.

Another means for increasing the amount of drug administered and thereby obtaining the desired effect involves increasing the surface area contact of the delivery system with the skin. Although an increase in the surface area will increase the amount of drug delivered to the patient, there are, of course, practical limitations with respect to increasing this surface area. The cost of producing very large delivery systems is prohibitive and patients are unlikely to wear a delivery system which has a surface such that it covers a large portion of the skin.

A completely different concept for increasing transdermal delivery of a pharmaceutically active drug depends on the incorporation of one or more skin penetration enhancers in the drug delivery system. Use, however, of such enhancers is subject to certain limitations, for example penetration enhancers should be dermatologically acceptable and compatible with the pharmaceutically active drug as well as the delivery system into which it is incorporated.

Numerous patents and publications have disclosed that penetration enhancers are generally useful in delivering nitroglycerin transdermally. However, the penetration enhancers of the present invention are unexpectedly superior to those previously known.

U.S. Pat. No. 4,291,015 to Keith, et al., shows the general state of the transdermal delivery art, and in particular, discloses the use of a polymeric diffusion matrix for the sustained release of pharmaceutically active drugs. The matrix is covered by a backing layer and applied to the skin where diffusion of the drug occurs and the drug is transdermally delivered to the patient.

U.S. Pat. No. 4,409,206 discloses a related transdermal delivery system, wherein the drug is dispersed within an adhesive (see also U.S. Pat. No. 4,390,520). In accordance with this system, the drug is dispersed in a pressure-sensitive adhesive which adheres to the skin during use. The drug simply diffuses from the adhesive and is absorbed through the skin.

U.S. Pat. No. 4,751,087 discloses the use of butyl stearate, ethyl oleate and equivalent fatty acid esters containing 14 to 20 carbon atoms in combination with glyceryl monolaurate as penetration enhancers in the transdermal delivery of nitroglycerin.

European Patent Application 123,948 published on Nov. 7, 1984 discloses the use of 1-pyroglutamyloxy-2,3-dihydroxypropane as a penetration enhancer for the transdermal delivery of nitroglycerin.

U.S. Pat. No. 3,711,602 discloses the use of dimethyl sulfoxide (DMSO) as a penetration enhancer for numerous medicaments, one of which is nitroglycerin.

European Patent Application 179,277 published on Apr. 30, 1986 discloses the use of dialkyl phosphates as penetration enhancers for coronary vasodilators such as nitroglycerin.

European Patent Application 196,769 published on Oct. 8, 1986 discloses transdermal patches comprised of certain preferred silicone polymer matrices and an adhesive layer comprising a skin penetration enhancer. Certain particular penetration enhancers are disclosed as having slight penetration enhancing activity, but are indicated to be inferior to the numerous esters disclosed. No mention is made of in vivo blood levels achieved through the use of selected penetration enhancers.

British Patent Application no. 2,081,582A published on Feb. 24, 1982 discloses the use of a silicone polymeric backing layer in combination with a hydrophobic solvent system (e.g. mineral oil) to enhance nitroglycerin penetration.

PCT Application no. 86/02052 published on Apr. 9, 1987 (pub. No. W087/01935) discloses the use of 1-dodecanoyl hexahydro-1H-azepine as well as related compounds for transdermal penetration enhancement.

More recently, there have been teachings with respect to the use of oleic acid as a penetration enhancer. (See Cooper, Eugene, R., "Increased Skin Permeability for Lipophilic Molecules" Journal of Pharmaceutical Sciences, volume 73, number 8, August 1984.) Cooper discloses the use of oleic acid in different concentrations in the presence of propylene glycol as a solid. Oleic acid does appear to enhance penetration of the active ingredient salicylic acid. Cooper also discloses the use of oleic acid in combination with 1,2-butanediol. The article specifically indicates that "other diols also exhibit this synergism with lipids, but the effects are less pronounced as the chain length is increased". Cooper teaches that the treatment of the skin with surfactants can have a substantial influence on increasing the penetration of polar molecules. However, such surfactants do not generally increase the transdermal penetration of non-polar molecules. Accordingly, Cooper appears to teach only the use of small amounts of oleic acid either alone or in combination with diols of short chain length and contains no teachings with respect to the use of large amounts of oleic acid alone or in combination with long chain diols and actually teaches against the use of such long chain diols.

U.S. Pat. No. 4,305,936 discloses a solution for topical or local application comprised of a corticosteroid in a carrier. The carrier is comprised of 1 to 4% by weight of solubilizing agents of a glycerol ester of a fatty acid containing 6 to 22 carbon atoms, 10 to 50% by weight of an alkanol cosolvent and from 20 to 50% by weight of water. The patent also indicates that the carrier can include other "non-essential ingredients" such as a suitable auxiliary adjuvant in an amount of up to 10% by weight. Oleic acid is mentioned as a suitable auxiliary adjuvant. The patent does not appear to contain any teaching with respect to the effect oleic acid might have on enhancing penetration and does not appear to contain any teachings with respect to the use of large amounts of oleic acid alone or in combination with a long chain diol.

Oleic acid has been used as a vehicle in which salicylic acid and carbinoxamine have been incorporated. See "Percutaneous Absorption of Drugs From Oily Vehicles" Washitake, et al., *Journal of Pharmaceutical Sciences, Vol.* 64, No. 3, pages 397-401. Washitake, et al. demonstrate that the effect of oleic acid varies depending on the active ingredient. Therefore, it is not possible to accurately predict which pharmaceutically active compounds might have their skin penetration enhanced by the use of oleic acid.

U.S. Pat. No. 4,455,146 discloses a plaster comprised of a thermoplastic elastomer dissolved in an oil or higher fatty acid, a tack-providing resin and an active ingredient. The "higher fatty acid" may be present in the range of 25 to 370 parts by weight per 100 parts by weight of the thermoplastic elastomer. The active ingredient may be present in an amount in the range of 0.09 to 110 parts by weight per 100 parts by weight of the thermoplastic elastomer, (see column 4, lines 3-35). Oleic acid is mentioned as "one of the preferred" higher fatty acids, (see column 3, lines 16-17).

European Patent Application 43,738, published Jan. 13, 1982, discloses enhanced skin penetration of lipophilic compounds using binary vehicles containing a $C_3$-$C_4$ diol, diol ester or diol ether (including butanediol) and a cell-envelope disrupting compound, e.g., a compound $R^3$-X wherein $R^3$ can be a non-terminal alkenyl of 7-22 carbons and X=OH (such as oleic, linoleic or linolenic acid).

PCT Publication No. 87/03490, published Jun. 18, 1987, discloses transdermal delivery of drugs using as a penetration enhancer 2-ethyl-1,3-hexanediol and/or oleic acid, wherein the preferred concentration of oleic acid is 5%.

U.S. Pat. No. 4,537,776 discloses the transdermal delivery of drugs using a combination of a) N-methylpyrrolidone, pyrrolidone or N-(2-hydroxyethyl)pyrrolidone, preferably the latter, and b) a cell-envelope disordering compound such as oleic acid or oleyl alcohol, wherein the ratio of a to b is 1:5 to 500:1.

U.S. Pat. No. 4,557,934 discloses a penetration-enhancing vehicle comprised of 1-dodecyl-azacycloheptan-2-one (i.e., Azone ®, commercially available from Nelson Research and Development, Co., Irvine, Calif.) in combination with a $C_3$-$C_4$ diol or an N-substituted azacycloalkyl-2-one such as N-methyl-2-pyrrolidone.

European Patent Application 267,617, published May 18, 1988, discloses penetration-enhancing vehicles comprising a combination of a lower alkanol, e.g. ethanol, and a cell-envelope disordering compound such as oleic acid or oleyl alcohol.

U.S. Pat. No. 4,322,433 discloses a sustained release biphasic cream carrier suitable for nitroglycerin. The components include a $C_8$-$C_{18}$ aliphatic alcohol and a hydrophilic component, e.g. water or propylene glycol, in a ratio which provides a specific hydrophilic/lipophilic balance value.

Although some percutaneous penetration enhancers are known, there remains a need for an enhancer which significantly increases the rate of transdermal delivery of a pharmacologically active drug to a patient.

Other types of transdermal delivery systems are known and each has its various advantages and disadvantages with respect to the transdermal delivery of different types of pharmaceutically active drugs. None of the conventional formulations provide the flux seen with the present invention, wherein in vitro results show about a two-fold increase and the in vivo results show about a four-fold increase in penetration over commercial transdermal nitroglycerin formulations.

SUMMARY OF THE INVENTION

The present invention relates to a transdermal nitroglycerin patch comprising a vasodilating-effective amount of nitroglycerin in combination with a carrier, said carrier comprising N-methyl-2-pyrrolidone, alone or in combination with at least one skin penetration enhancer selected from the group consisting of oleic acid, linoleic acid, isopropyl linoleate (e.g., Ceraphyl TM IPL, from Van Dyk Division of Mallinckrodt, Inc., Belleville, N.J.), oleyl alcohol, 1-dodecyl-azacycloheptan-2-one and butanediol. When N-methyl-2-pyrrolidone is combined with another skin penetration enhancer, the combination of N-methyl-2-pyrrolidone and oleic acid is preferred.

Another aspect of the invention encompasses a transdermal nitroglycerin patch comprising a vasodilating-effective amount of nitroglycerin in combination with a carrier, said carrier comprising at least one skin penetration enhancer selected from the group consisting of oleyl alcohol, linoleic acid, isopropyl linoleate, butanediol, 1-dodecyl-azacycloheptan-2-one and oleic acid, provided that when 1-dodecyl-azacycloheptan-2-one or oleic acid is present, a second penetration enhancer must be present. A carrier comprising oleyl alcohol as the sole penetration enhancer is preferred.

Yet another aspect of the invention is a novel transdermal nitroglycerin patch comprising two or more regions, for example two regions, wherein one region is comprised of a combination of a vasodilating-effective amount nitroglycerin, a pressure sensitive adhesive and at least one penetration enhancer selected from the group consisting of N-methyl-2-pyrrolidone, oleic acid and 1-dodecyl-azacycloheptan-2-one, and the other region is comprised of a vasodilating-effective amount of nitroglycerin and a penetration enhancer selected from N-methyl-2-pyrrolidone and oleyl alcohol.

The invention further includes a novel transdermal nitroglycerin patch as described above, wherein the regions are separated from each other by an area of impermeable backing material. A preferred patch comprises two regions, a center region and an outer region.

The invention in still another aspect relates to treatment of a mammal such as a human comprising administering a vasodilating effective amount of nitroglycerin to a human in need of such treatment, wherein the treatment comprises applying to the skin of said human a transdermal patch as described above.

DETAILED DESCRIPTION

As used herein, the term "transdermal" is used in its conventional sense, and means the introduction and delivery of a pharmacological or medicinal compound through the skin of a patient in need of such treatment to elicit a systemic effect. Hence, transdermal delivery of a drug is effective for treating illnesses, conditions or disorders beyond mere topical applications of a medicinal agent. The transdermal system described herein is useful for the delivery of nitroglycerin to elicit a vascular dilatory effect.

The amount of nitroglycerin which can be delivered transdermally can be increased through the use of penetration enhancers. In order for a compound to be useful as a percutaneous penetration enhancer, the compound must meet a number of different requirements. First, the compound must be dermatologically acceptable, such that when used topically, it does not cause unacceptable adverse reactions, e.g. local irritation or swelling. Second, the penetration enhancer must be compatible with nitroglycerin and the other components (e.g. the polymeric adhesives or matrices) of the transdermal delivery system. If the penetration enhancer and nitroglycerin are incompatible, separation of ingredients or a chemical reaction may take place, rendering the nitroglycerin inactive or non-absorbable. Third, it is preferable for the penetration enhancer to have been approved for human medicinal use.

The transdermal patch described herein is any conventional patch from, e.g., adhesive matrix, polymeric matrix or reservoir patch, and is generally comprised of one or more backing layers, adhesive, nitroglycerin, one or more penetration enhancers, an optional rate controlling membrane and a release liner which is removed to expose the adhesive prior to application. Polymeric matrix patches also comprise a polymeric-matrix forming material.

The backing layer used herein may be any conventional transdermal backing material which does not adversely react with the nitroglycerin or the other components in the patch. Examples are foam, metal foil, polyester, low density polyethlene, copolymers of vinyl chloride and polyvinylidine chloride and laminates thereof. A water resistant polyethylene or vinyl is preferred.

The adhesive used in the patch described herein may be any pharmaceutically acceptable pressure sensitive polymeric adhesive, such as an acrylic, vinyl acetate, silicone or synthetic or natural rubber adhesive. For example, acrylic adhesives such as RA 2484, RA 2333, RA 2397, R 363 and R 362 from Monsanto Co. are appropriate. Other acrylic adhesives, such as Durotak®, manufactured by Morton Thiokol, Inc., and Neocryl TM XA5210 by Polyvinyl Chemicals, Ltd. may be utilized.

Numerous silicone based adhesives may be used, such as Q72929, Q27406, X72920 and 355, each manufactured by Dow-Corning.

Vinyl acetate adhesives include Flexcryl 1614, 1617, 1618 and 1625 from Air Products. Natural and synthetic rubber adhesives include polyisobutylenes, neoprenes, polybutadienes and polyisoprenes.

The adhesives may be used singly or combined in the patch.

The adhesive material may also be modified through the use of diluents or thickeners, if necessary. The preferred diluents are organic or inorganic solvents such as ethanol or water. The preferred thickeners include acrylic polymer thickeners such as Union Amsco RES 6038 by Unocal. Thickeners are used to adjust viscosity of the adhesive mixtures to about 6,000–10,000 cps for coating on the backing material. A crosslinking agent such as Aerotex Resin 3730 (American Cyanamid) may be added to facilitate curing.

Examples of polymeric matrix materials are polyvinyl alcohols, polyvinyl pyrrolidones, gelatin and partially hydrolyzed polyvinyl alcohols. Other agents may be incorporated into the matrix material, such as gelling agents, e.g., Klucel TM, povidone or gelatin, or hygroscopic agents, e.g., glycerin, sorbitol or glycols. Such agents make the matrix material easier to handle and affect the rate of nitroglycerin delivery.

Materials suitable for rate-controlling membranes include ethylene-vinyl acetate (EVA) copolymer membranes (e.g. 1–20% vinyl acetate), polyvinylalcohol (PVA) gels and silicone films.

Protective release liners used to prevent dirt from sticking to the patch during shipment and storage are made from such materials as polyethylene and polyethylene coated paper, polystyrene and polycarbonates, preferably silicon-coated to facilitate removal.

The skin penetration enhancers used herein include one or more of the following: N-methyl-2-pyrrolidone, 1-dodecyl-azacycloheptan-2-one, oleic acid, oleyl alcohol, linoleic acid, isopropyl linoleate and butanediol, each at selected concentrations when used alone or in combination to increase flux.

As used herein, the term "% concentration" relates to the ratio of the weight of the particular ingredient relative to the total patch weight. Total patch weight refers to the weight of the adhesive matrix, the polymeric matrix or the contents of the reservoir, but does not include the weight of the backing material, release liner or rate-controlling membrane.

When N-methyl-2-pyrrolidone is used as a penetration enhancer, it may be present in an amount ranging from about 5 to about 30 percent concentration. The preferred concentration of N-methyl-2-pyrrolidone when used as the sole penetration enhancer is 10 to 20 percent. The preferred concentration of N-methyl-2-pyrrolidone when used in combination with other penetration enhancers is 10 percent.

When oleic acid is used herein as a penetration enhancer, it is used at a 2.5 to 10 percent concentration in combination with N-methyl-2-pyrrolidone, 1-dodecyl-azacycloheptan-2-one, linoleic acid or isopropyl linoleate. The preferred concentration of oleic acid when used herein is 10 percent.

When 1-dodecyl-azacycloheptan-2-one is used as the penetration enhancer in the invention, it generally ranges in concentration from 5 to 20 percent, and is used in combination with N-methyl-2-pyrrolidone, oleic acid or oleyl alcohol. The preferred concentration of 1-dodecyl-azacycloheptan-2-one when used herein is 10 percent.

When oleyl alcohol is used herein as a penetration enhancer, it is used at 5 to 20% concentration, preferably about 10% concentration, alone or in combination with other penetration enhancers.

Similarly, linoleic acid, when present, is used at a 5 to 15% concentration, with 10% being preferred, and butanediol, when present, is used at 2–10% concentration, with 5% being preferred. Preferably, when present, linoleic acid and butanediol are used in combination, at concentrations of 10% and 5%, respectively.

When present, isopropyl linoleate is used at a concentration of about 5 to 30%, with about 10% being preferred.

Preferred skin penetration enhancers are oleyl alcohol alone at 10% concentration, and a combination of N-methyl-2-pyrrolidone at 10% concentration and oleic acid at 10% concentration.

Adhesive matrix transdermal devices are preferred and methods for preparing them are known in the art. A preferred method for preparing adhesive matrix transdermal devices of the present invention comprises casting a thin layer of the polymer blend (i.e., the mixture of adhesive, active, skin penetration enhancer and adhesive diluents or thickeners) onto the material to be used as the release liner, curing the polymer blend to form the polymer adhesive (including drying in an oven), and laminating the backing material to the resultant adhesive layer. Suitably sized patches may then be punched out automatically, and the patches are preferably sealed into protective pouches.

The layer of polymer blend cast on the release liner according to the preferred method is preferably about 5 mils to about 10 mils thick. The cast layer is preferably dried at a temperature of about 80° C. for a period of about 20 min. A specific example of a formulation is shown below.

Polymeric matrix transdermal patches are also prepared by known methods. When a polymeric matrix is present, the adhesive can be used to coat the backing layer and to adhere the polymeric matrix to the backing-layer, leaving an adhesive margin around the polymeric matrix in order to affix the patch to the skin while allowing the drug to transfer directly from the matrix to the skin. Alternatively, the polymeric matrix can be glued to the backing and adhesive may be coated on the backing around the matrix.

Reservoir-type patches may also be made by known procedures. For example, a layer of adhesive may be applied to the release liner, the rate-controlling membrane may be laminated to the adhesive side, a portion of a solution comprising nitroglycerin and one or more penetration enhancer (e.g., the polymer blend) may be placed on the membrane, and the backing material may then be heat-sealed to the rate-controlling membrane around the edges of the patch.

Representative examples of formulations which generate unexpectedly superior flux for nitroglycerin transdermal patches are described in the examples below.

EXAMPLE 1

Adhesive Matrix

| Component | % (w/w) |
| --- | --- |
| acrylic adhesive | 37.4 |
| acrylic polymer thickener | 2.6 |
| N-methyl-2-pyrrolidone | 10 |
| oleic acid | 10 |
| nitroglycerin | 40 |
| | 100 |

Method of Manufacture

Combine the adhesive, the penetration enhancers, the thickener and the nitroglycerin and mix until smooth. Check the viscosity, and if necessary, add thickener to increase the viscosity of the adhesive blend to the required level.

Cast a 5-10 mil layer of polymer blend onto the release liner. Dry the layer at 80° C. for 20 min. Laminate the backing material to the dry polymer film using conventional equipment.

Using an automatic punch machine, punch out the desired size patches. Using a pouch machine, enclose the patches in pouches and heat-seal closed.

EXAMPLE 2

Adhesive Matrix

| Component | % (w/w) |
| --- | --- |
| acrylic adhesive | 47.4 |
| acrylic polymer thickener | 2.6 |
| oleyl alcohol | 10.0 |
| nitroglycerin | 40.0 |
| | 100.0 |

Use the procedure described in Example 1.

EXAMPLE 3

Adhesive Matrix

| Component | % (w/w) |
| --- | --- |
| acrylic adhesive | 42.4 |
| acrylic polymer thickener | 2.6 |
| linoleic acid | 10.0 |
| butanediol | 5.0 |
| nitroglycerin | 40.0 |
| | 100.0 |

Use the procedure described in Example 1.

EXAMPLE 4

Adhesive Matrix

| Component | % (w/w) |
| --- | --- |
| acrylic adhesive | 34.8 |
| silicone adhesive | 3.9 |
| acrylic polymer thickener | 1.3 |
| m-pyrol | 10.0 |
| oleic acid | 10.0 |
| nitroglycerin | 40.0 |
| | 100.0 |

Use the procedure described in Example 1.

EXAMPLE 5

Polymeric Matrix

| Component | % (w/w) |
| --- | --- |
| glycerin | 11.5 |
| polyvinyl alcohol | 25.3 |
| polyvinyl pyrrolidone | 3.1 |
| nitroglycerin | 22.0 |
| oleyl alcohol/oleic acid | 10.0 |
| water | 28.1 |
| | 100.0 |

Method of Manufacture

Combine glycerin and water and heat to 90° C.; after reaching at least 70° C., slowly add polyvinyl alcohol and polyvinyl pyrrolidone, then stir at 90° C. until dissolution is complete. Add oleyl alcohol and oleic acid, stir, add nitroglycerin and stir until thoroughly mixed.

Pour mixture into glass or stainless steel forms to produce a matrix having a thickness of about 3 to 4 mm. Allow the matrix to dry for 10-60 minutes, then cut into the desired size and adhere to backing material.

The results of in vitro flux testing, demonstrating unexpected superiority of the formulations described herein, are shown below in Table 1 (m-pyrol is another name for N-methyl-2-pyrrolidone). The flux rate ($\mu g/cm^2/hr$) of nitroglycerin from different transdermal patches was measured through heat isolated human cadaver epidermis using single compartment diffusion cells.

TABLE 1

| | Flux (mcg/cm$^2$/hr) | | |
|---|---|---|---|
| | Trial 1 | Trial 2 | Trial 3 |
| 40% nitroglycerin in acrylic adhesive without pentration enhancers | 11.3 ± 0.5 | 7.6 ± 2.07 | 8.9 ± 2.6 |
| Pentration Enhancers | | | |
| m-pyrol 10% | 21.1 ± 3.1 | 12.4 ± 0.36 | N.T. |
| m-pyrol 15% | N.T. | 13.2 ± 2.7 | N.T. |
| m-pyrol 20% | 17.5 ± 1.96 | N.T. | N.T. |
| oleyl alcohol 10% | N.T. | N.T. | 17.0 ± 0.3 |
| linoleic acid 10% plus butanediol 5% | N.T. | N.T. | 16.7 ± 3.3 |
| m-pyrol 10% plus oleic acid 2.5% | N.T. | N.T. | 16.2 ± 1.5 |
| m-pyrol 10% plus oleic acid 5% | N.T. | N.T. | 17.7 ± 3.1 |
| m-pyrol 10% plus oleic acid 10% | N.T. | 29.7 ± 5.56 | N.T. |

From the results above in Table 1, one can see that the formulations described herein provide unexpectedly superior flux enhancement over the standard (i.e., no penetration enhancer).

To treat a patient in need of coronary vasodilation using a patch described herein, the clinician should take into account the severity of the condition being treated as well as the age, weight and overall condition of the patient. The clinician then selects a particular patch for application to the skin of the patient, which contains and will deliver the amount of nitroglycerin desired. For example, a typical nitroglycerin patch described herein may contain from about 5 to about 120 mg of nitroglycerin, preferably about 40 mg, and may have an area of about 5 to about 20 cm$^2$, preferably about 10 cm$^2$. One patch is applied to the skin of a patient and is removed and replaced after 24 hours to effect essentially continuous coronary vasodilation. Of course, the patient may alternatively be instructed to use a lesser or greater number of patches, to allow a period of time between patches or other unique clinical modifications to the regimen described above, as determined by the clinician.

Another aspect of the present invention arises from the unique absorption profile of nitroglycerin demonstrated from the instant transdermal patches. The currently marketed nitroglycerin patches demonstrate a zero order absorption of drugs, but the present patch provides a constantly changing absorption profile which yields a curved profile as opposed to a prolonged plateau effect. This curved profile shows that blood levels rise for 12-14 hours, remain steady for a time, then decrease. It has recently been suggested that dosing from the current commercial patches may lead to tolerance of the drug, and that provisions should be made for intermittent dosing, e.g. the patch should be removed and no drug be administered for some period of time (preferably overnight) in each 24-hour period. The present patch in effect provides such an intermittent dose without requiring removal of the patch at a certain time, thereby improving patient compliance.

In another aspect of the instant invention, the transdermal patch formulations previously described may be combined in a single patch configuration which allows the formulations to function separately from each other. For example, a concentric ring patch having a center and an outer area is one such patch. The use of such a patch, and the unexpected superiority in flux enhancement generated by this dual-formulation patch, are exemplified below in Table 2. It is noted that in Table 2, the patches tested were of equal surface area, and the surface area of the center and outer ring areas were maintained constant.

TABLE 2

| | | Flux ($\mu g/cm^2/hr$) | |
|---|---|---|---|
| Control | | Trial 1 | Trial 2 |
| Nitroglycerin 40% in acrylic adhesive without penetration enhancers | | 4.8 ± 0.6 | 5.1 ± 0.6 |
| Formulations with Penetration Enhancers | | | |
| Center | Outer Ring | | |
| Oleic Acid 10% plus m-pyrol 10% | Oleyl alcohol 10% | 16.3 ± 0.8 | 23.1 ± 3.8 |
| oleic acid 10% plus m-pyrol 10% | None | 8.7 ± 0.5 | N.T. |

From the data above, it is clear that a transdermal nitroglycerin patch using the penetration enhancers as described herein provides unexpectedly superior flux enhancement over prior formulations.

We claim:

1. An adhesive, polymeric matrix or reservoir transdermal patch comprising a vasodilating-effective amount of nitroglycerin and a carrier, said carrier comprising N-methyl-2-pyrrolidone and oleic acid, wherein the polymeric matrix comprises one or more polymeric matrix forming materials selected from the group consisting of polyvinyl alcohols, polyvinyl-pyrrolidones, gelatin and partially hydrolyzed polyvinyl alcohols.

2. A transdermal nitroglycerin patch of claim 1 comprising N-methyl-2-pyrrolidone in an amount of from about 5 to about 30 percent of the total patch weight and oleic acid in an amount of from about 2.5 to about 10 percent of the total patch weight.

3. An adhesive transdermal patch of claim 1 comprising 37.4 percent acrylic adhesive, 10 percent N-methyl-2-pyrrolidone, 10 percent oleic acid and 40 percent nitroglycerin.

4. A method of administering a vasodilating effective amount of nitroglycerin to a human in need of such treatment comprising applying to the skin of said human a transdermal patch of claim 1.

5. A transdermal nitroglycerin patch comprising a vasodilating effective amount of nitroglycerin divided between two regions separated by an area of impermeable backing material, one region comprising nitroglycerin and a first carrier, which first carrier comprises N-methyl-2-pyrrolidone in an amount of from about 5 to about 30 percent of the total patch weight and oleic acid in an amount of from about 2.5 to about 10 percent of the total patch weight, and the other region comprising nitroglycerin and a second carrier, which second carrier comprises oleyl alcohol in an amount of from about 5 to 20 percent of the total patch weight.

6. A method of administering a vasodilating effective amount of nitroglycerin to a human in need of such treatment comprising applying to the skin of said human a transdermal patch of claim 5.

* * * * *